United States Patent [19]
Ungless et al.

[11] Patent Number: 6,129,663
[45] Date of Patent: Oct. 10, 2000

[54] MONITOR FOR INPUT OF SUBJECTIVE RATING SCORES

[75] Inventors: Gary Steven Ungless; Nigel Robert Oakley, both of Cambridge, United Kingdom; Dennis M. Ebner, Sisters, Oreg.

[73] Assignee: Mini-Mitter Co., Inc., Sunriver, Oreg.

[21] Appl. No.: 09/312,918

[22] Filed: May 17, 1999

[51] Int. Cl.[7] .................................................. A61B 5/00
[52] U.S. Cl. ............................................................ 600/300
[58] Field of Search ................................. 600/300, 557, 600/587, 595

[56] References Cited

U.S. PATENT DOCUMENTS

| | | | |
|---|---|---|---|
| 5,642,731 | 7/1997 | Kehr | 600/300 |
| 5,692,500 | 12/1997 | Gaston-Johansson | 600/300 |
| 5,719,825 | 2/1998 | Dotter | 600/300 |
| 5,908,383 | 6/1999 | Brynjestad | 600/300 |
| 5,954,641 | 9/1999 | Kehr et al. | 600/300 |

*Primary Examiner*—Max Hindenburg
*Attorney, Agent, or Firm*—John Smith-Hill; Smith-Hill and Bedell

[57] ABSTRACT

Score values representing a user's subjective rating of a condition as recorded using a monitor worn by or secured to the user. The monitor includes a clock for generating a periodic timing signal, a user interface for entering score values and a transducer for prompting the user to enter a score value. A time storage device stores timing information and a data storage device for stores time values and related score values. A controller activates the transducer at times indicated by the timing information. The stored time values and related score values can be read from the data storage device.

12 Claims, 3 Drawing Sheets

MONITOR FOR INPUT OF SUBJECTIVE RATING SCORES

BACKGROUND OF THE INVENTION

This invention relates to a monitor for input of subjective rating scores.

It is desirable that a doctor should know with some degree of reliability the efficacy of the treatment regime that he has prescribed in order to allow the doctor to determine whether the treatment should be adjusted. The doctor will generally ask the patient whether the treatment regime has been helpful, for example in relieving pain, but the reliability of the patient's response could be affected by passage of time and imperfect recollection. It would be helpful to have the patient keep a diary showing the efficacy of the treatment as a function of time so that the doctor can observe any correlation between the patient's scores and, for example, the time at which the patient takes medication, but this is inconvenient for the patient and the validity of the entries in the diary can be impaired if, for example, the patient does not make the entries at the proper times but relies on recollection to make several entries at one time.

SUMMARY OF THE INVENTION

In accordance with the present invention there is provided an apparatus to be worn by or secured to a user for recording score values representing a user's subjective rating of a condition, comprising a clock for generating a periodic timing signal, a user interface for entering score values, a transducer for prompting the user to enter a score value, a time storage device for storing timing information, a data storage device for storing time values and related score values, a controller coupled to said clock, said time storage device and said transducer for activating said transducer at times indicated by said timing information, and an output means for reading the stored time values and related score values from the data storage device.

A typical application of a monitor in accordance with the invention is for pain therapy where a doctor might wish to use a record of the patient's level of perceived pain to aid in determining an appropriate dosage of pain relief medication. The doctor would program the monitor with selected times for the patient to input subjective pain scores. The selected times might be expressed simply as an interval between each two consecutive input times. The monitor sounds an audible prompt at each selected input time and the patient inputs a score in response to each prompt. The patient may also input a score independent of the prompt, for example because of acute pain. The monitor stores each score and the time it was input. At the end of a data collection period, the doctor retrieves the monitor and downloads the information to a computer. The doctor interprets the information to determine whether the dosage should be adjusted.

It has been suggested that a patient's subjective impression of certain conditions depends on the level of the patient's physical activity. The correlation between a person's physical activity and his impression of a condition gives a doctor a better understanding of the patient's condition and provides a means of normalizing data from patient to patient. Accordingly, in a preferred embodiment the monitor also provides a means for periodically measuring the physical activity level of the patient and the time at which the activity level was measured and recording both the activity level and the time at which the activity level was measured.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Figure 1:
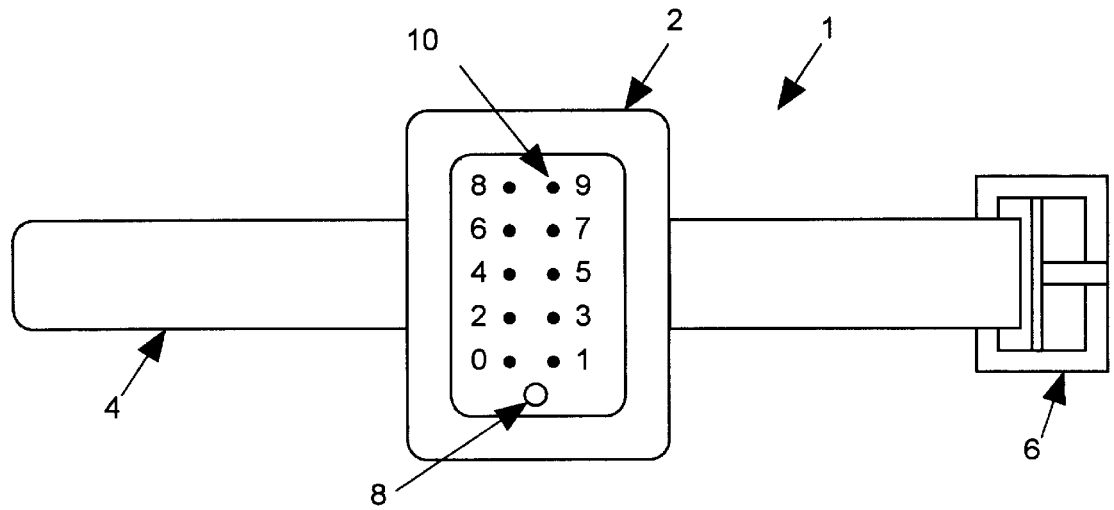
FIG. 1 is a perspective view of a programmable monitor which allows the input of subjective rating scores.
Figure 2:
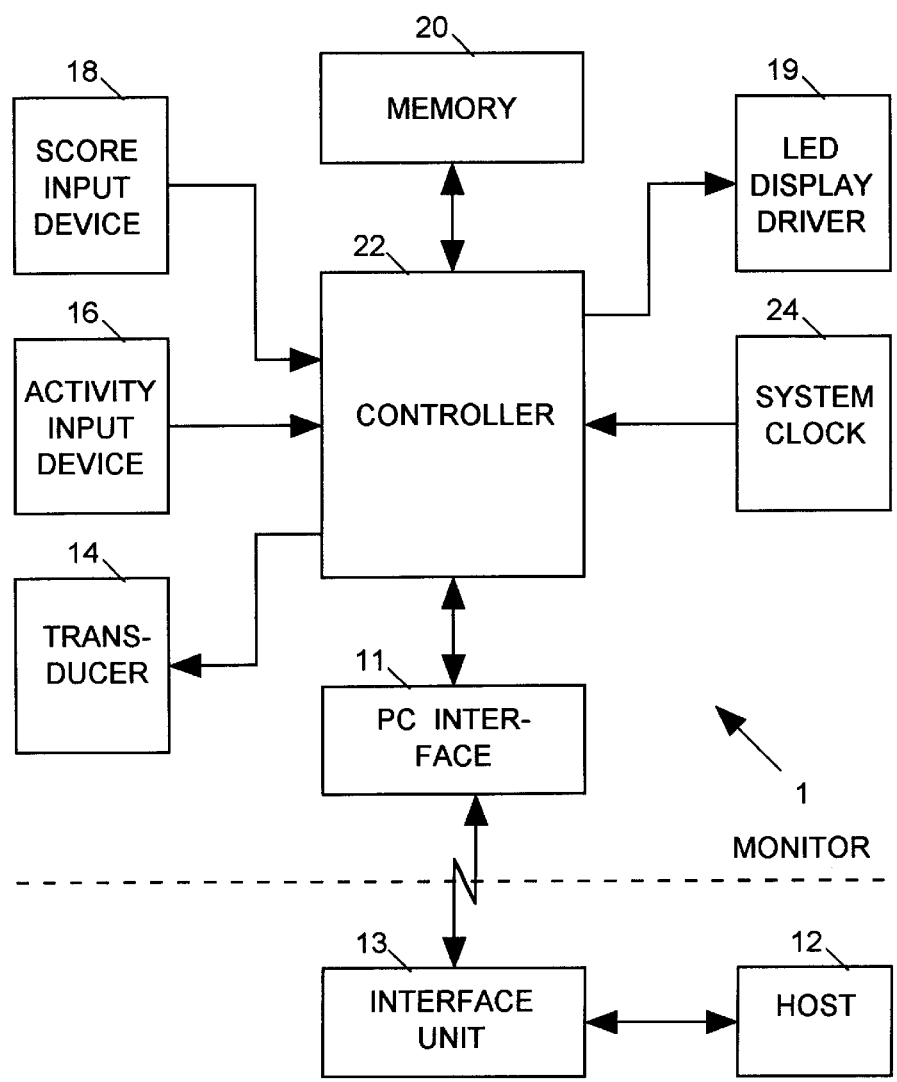
FIG. 2 is a block diagram illustrating the main functional components of the monitor.

The illustrated monitor 1 provides a means for recording a patient's subjective impression of a condition such as pain or depression. Referring to FIG. 1, the monitor 1 comprises a casing 2 containing the operative components of the monitor and a strap 4 with a buckle 6 to allow the monitor to be worn on a patient's wrist. Part of the external surface of the casing 1 functions as a patient interface panel. Within the patient interface panel there is a push button 8 and an array 10 of ten light emitting diodes (LEDs) having the numerals "0" through "9" inscribed adjacent the LEDs respectively.

The doctor instructs the patient to enter his subjective level of a condition, such as pain, each time the monitor provides an audible prompt by pressing the button 8 a number of times depending on the level of the condition. The doctor will typically instruct the patient to press the button once to indicate the mildest pain and nine times to indicate the most severe pain.

Monitor 1 has two main operating modes. In the data collection mode, monitor 1 collects subjective scores entered by the patient, generates audible prompts from time to time to induce the patient to enter a subjective score, and collects objective activity measurements. In the exchange mode, monitor 1 is linked to a host computer 12 for either uploading control information, such as program information for controlling the times at which prompts are given, from the host computer to the monitor or for downloading collected data from the monitor to the host computer for analysis.

The operative components of the monitor 1 include a memory 20 which stores timing information, a transducer 14 which generates the audible prompts based on the timing information stored in memory 20, a score input device 18 which provides score values for loading into the memory 20, an activity input device which provides activity level values for loading into the memory 20, and an LED display driver 19 for supplying operating current to the LEDs. Operation of the transducer 14, score input device 18, activity input device 16 and LED display driver 19 is controlled by a controller 22 and a system clock 24.

The monitor also includes a PC interface 11 for linking the controller 22 to the host computer 12 through an interface unit 13 for upload and download. The PC interface 11 is a wireless device and may operate in the manner described in co-pending patent application Ser. No. 09/212,834, the entire disclosure of which is hereby incorporated by reference herein.

The memory 20 has four address ranges. Locations in the first address range store initialization values, including a reference time value corresponding to the value of standard time or daylight savings time observed externally of the monitor at the time and place at which the monitor is programmed. Locations in the second address range store the timing information that specifies the times (relative to the reference time value) at which the transducer 14 is to be activated. In the case of the example that is described in detail herein, the timing information is composed of a succession of time interval values. The first time interval value specifies the interval between the time at which the monitor enters the data collection mode (relative time zero) and the time at which the first prompt is given, and each succeeding time interval value specifies the interval between the end of the preceding time interval and time at which the next prompt is given. The third address range stores score/time value pairs and the fourth address range stores activity level/time value pairs.

Before the start of a data collection session, the doctor links the monitor 1 to the host computer 12 via the PC interface 11 and the interface unit 13 and the monitor enters the exchange mode. In the exchange mode, the host computer supplies the reference time value and the time interval values to the controller 22, which loads them in the appropriate address ranges of the memory 20. The doctor removes the monitor from the interface unit and attaches the monitor to the patient's wrist. The monitor enters the data collection mode and the controller 22 reads a first time interval value from the memory 20. In the initial condition of the monitor, the controller disables the LED display driver 19.

Figure 3:
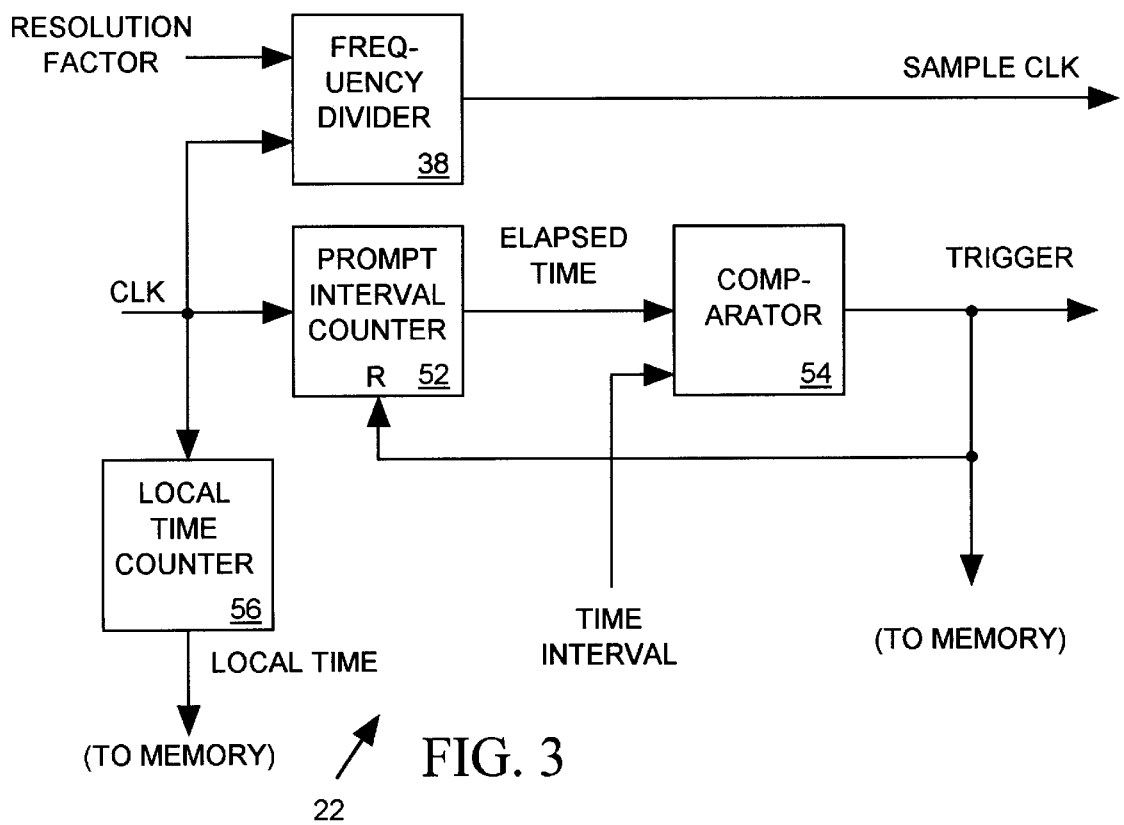
FIG. 3 is a more detailed partial functional block diagram of the controller shown in FIG. 2.

The system clock 24 generates a periodic signal CLOCK at a selected frequency and supplies the signal CLOCK to the controller 22. Referring to FIG. 3, the controller includes a comparator 54 which receives the first time interval value at one input as the value TIME INTERVAL. The controller 22 also includes a local time counter 56 which receives the signal CLOCK and counts the pulses of the signal CLOCK and provides the current value of its count as LOCAL TIME for the current data collection period. A prompt interval counter 52 counts the pulses of the signal CLOCK after being reset and provides the value as ELAPSED TIME to a comparator 54, which compares ELAPSED TIME with TIME INTERVAL. If ELAPSED TIME is equal to TIME INTERVAL, comparator 54 asserts a signal TRIGGER. In response to the signal TRIGGER, the controller activates the transducer 14, resets prompt interval counter 52 and reads the next TIME INTERVAL value from the second address range of memory 20. Activation of the transducer causes the monitor to issue an audible prompt. Further, the controller enables the LED display driver 19.

The controller also includes a programmable frequency divider 38 which provides a sampling clock signal by dividing the clock signal by a resolution factor which is loaded into the first address range of the memory 20 when the monitor is operating in the exchange mode.

Figure 4:
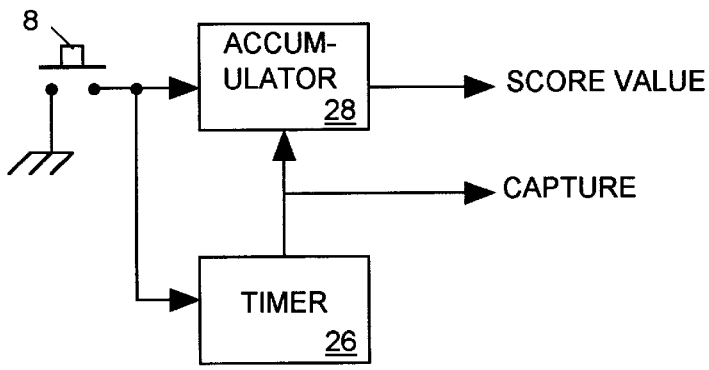
FIG. 4 is a more detailed block diagram of the score input device shown in FIG. 2.

Referring to FIG. 4, the push button 8 in the patient interface panel is part of the score input device 18 which provides score values for loading into the third address range of memory 20. The score input device also includes an accumulator 28 which accumulates the number of times the button 8 has been pressed and a resettable timer 26 which resets the accumulator 28 if a selected input window interval expires without the button 8 being pressed. Thus, assuming that the accumulator 28 is in the reset condition, the count stored in the accumulator is zero. When the button 8 is pressed, the count increases to one and the timer starts to time the input window interval. If the button is pressed again before the input window interval expires, the count increases by one, up to a maximum of nine, and the timer 26 is reset. If the input window interval expires without the button being pressed, the timer 26 resets the accumulator 28.

The controller employs the SCORE VALUE provided by the accumulator to control operation of the LED display 10. The controller includes a decoder (not shown) which receives the current SCORE VALUE and selects the appropriate LED in the range from "0" to "9" for illumination. For example, before the patient presses the button 8 for the first time after the prompt is given, SCORE VALUE is zero and an LED SELECT signal provided by the decoder causes the LED display driver 19 to illuminate the LED "0." When the patient presses button 8 for the first time, SCORE VALUE is one and the decoder selects the LED "1." The LED SELECT signal causes the LED display driver 19 to extinguish the LED numbered "0" and illuminate the LED "1." If the patient presses the button again before the input window interval expires, SCORE VALUE increases to two. The decoder selects the LED "2" and the LED SELECT signal causes the LED display driver to extinguish the LED numbered "1" and illuminate the LED numbered "2." Similarly, each time the patient presses the button 8 before the input window interval expires, or SCORE VALUE reaches nine, SCORE VALUE increases by one and the LED SELECT signal causes the LED display driver to extinguish the current LED and illuminate the next LED. The patient can thereby see from the patient interface panel how many times he has pressed the button 8 in the current input window.

When the input window interval expires, the decoder selects the LED "0" but the LED display driver is disabled and the currently illuminated LED is extinguished without another LED being illuminated.

The patient may also enter a score value without being prompted, e.g. in the event of particularly acute pain. The mode of operation is the same as when the score value is entered in response to a prompt except, of course, that the LED "0" is not illuminated immediately before the patient first presses the button 8 and consequently the LED "0" is not extinguished when the patient presses the button. Further, the controller enables the LED display device in response to the button 8 being pressed.

The reset signal that is supplied by the timer 26 for resetting the accumulator when the input window interval expires is also supplied to the controller 22 and causes the controller to capture the current SCORE VALUE provided by the accumulator 28 and the current LOCAL TIME value provided by local time counter 56. The controller loads the SCORE VALUE and the current LOCAL TIME value in the third address range of the memory 20.

It will be understood that if the patient does not press the button 8 in response to the prompt, the SCORE VALUE provided by the accumulator 28 when the input window interval expires will be zero. In this case, the LED "0" is extinguished when the input window interval expires.

Figure 5:
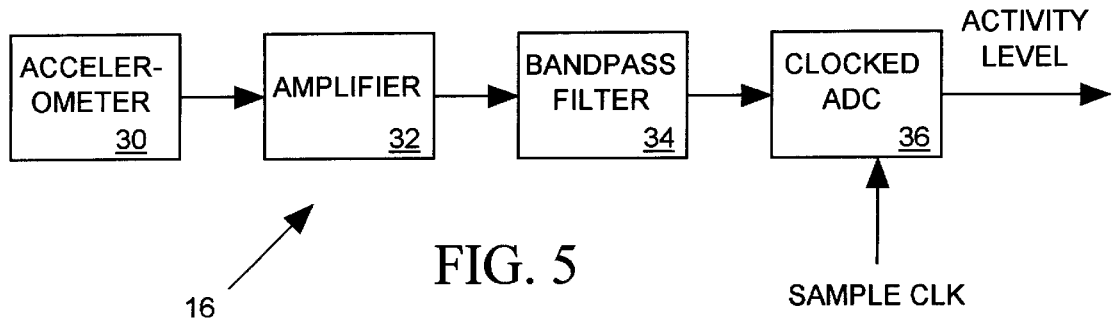
FIG. 5 is a more detailed block diagram of the activity input device shown in FIG. 2.

Referring to FIG. 5, the activity input device 16 includes an accelerometer 30 which senses the acceleration of monitor 1 and outputs a signal proportional to the amount and duration of the acceleration. The activity input device 16 may be as described in copending patent application Ser. No. 09/212,834. The accelerometer 30 is a piezo-ceramic device oriented within the casing 2 of monitor 1 to sense acceleration of the patient's wrist. The acceleration sensed by accelerometer is quite a good indicator of the level of the patient's activity. The acceleration signal generated by the accelerometer is amplified by an amplifier 22 and filtered by a bandpass filter 34 to remove frequencies outside the range from 2 Hz to 11 Hz. These frequency limits may be varied to some extent but experiment indicates that this range of frequencies reflects the normal range of movements of the wrist. The signal provided by the filter 34 is provided to an analog-to-digital converter (ADC) 36 which samples the filtered signal under control of the signal SAMPLE CLK provided by the frequency divider 38 and quantizes the sample as ACTIVITY LEVEL. The controller captures the value of ACTIVITY LEVEL provided by the ADC 36 and the current value of LOCAL TIME and stores the ACTIVITY LEVEL and LOCAL TIME values in the fourth address range of the memory. Generally, the interval between acquisition of ACTIVITY LEVEL will be considerably shorter than the interval between prompts and may, for example, be from 2 seconds to 15 minutes.

At the end of a data collection session, the third and fourth address ranges of the memory 20 contain numerous score/time value pairs and numerous activity level/time value pairs. The doctor retrieves the monitor from the patient and connects it to the host computer through the PC interface 11 and the interface unit 13. The monitor enters the exchange mode, in which the host computer downloads the contents of the third and fourth address ranges of the memory 20 for analysis and interpretation. The host computer may also read the reference time from the first address range in order to allow external time values to be calculated from the relative time values read from the third and fourth address ranges. When the contents of the third and fourth address ranges have been downloaded, the host computer supplies reset commands to the controller 22, causing the controller to reset the local time counter 56 and otherwise initialize the monitor for a new data collection session.

Figure 6:
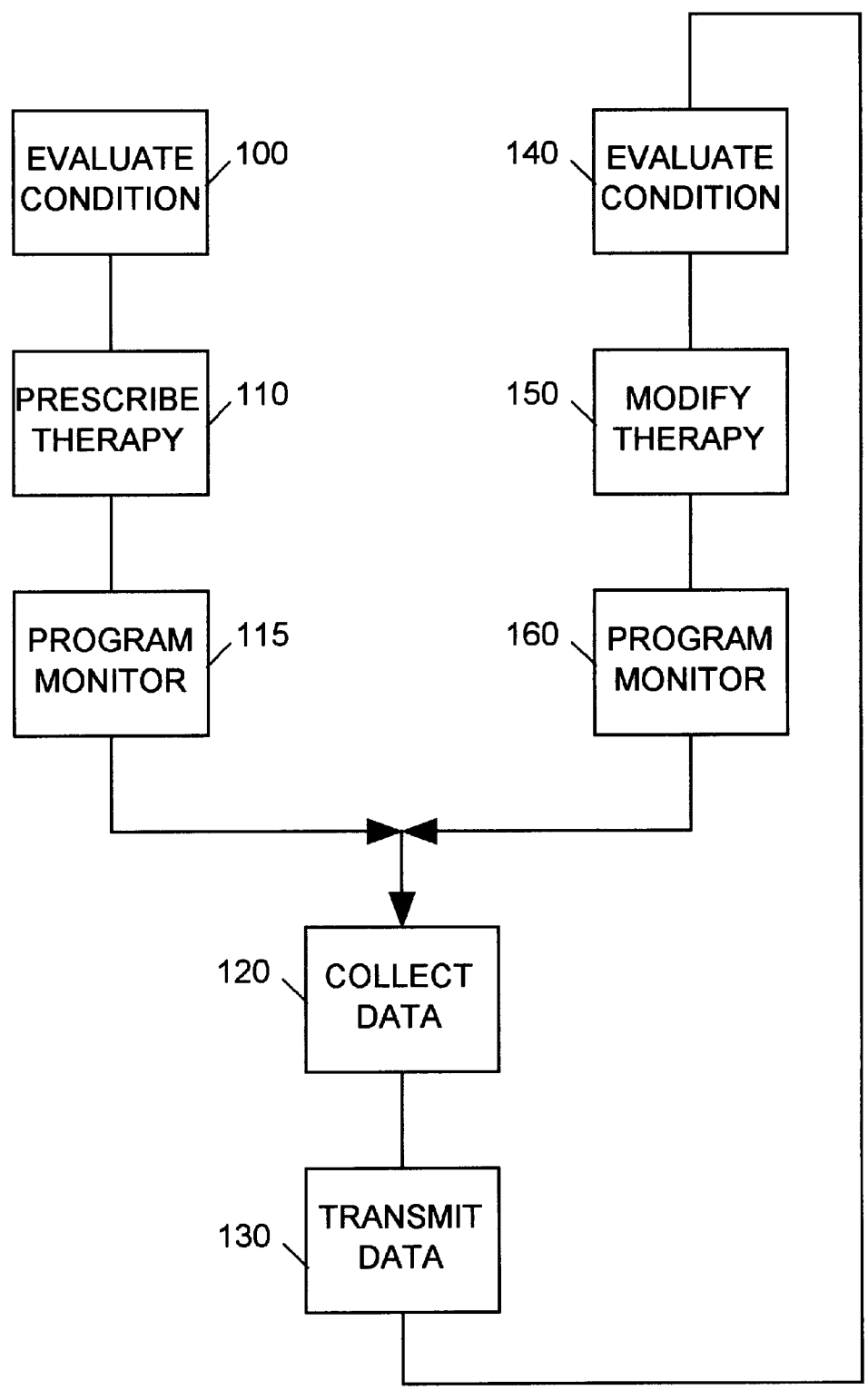
FIG. 6 is a flow chart illustrating use of the monitor shown in FIGS. 1–5 in remote diagnosis and therapy.

FIG. 6 illustrates a typical application of the monitor shown in FIGS. 1–5. Initially, a doctor examines the patient and evaluates the patient's condition (step 100). Based on direct observation of the patient, the doctor prescribes a therapy (step 110) and programs the monitor having regard to the patient's condition and the therapy (step 115). If, for example, the doctor prescribes pain relief medication to be taken at regular intervals, he might program the monitor to activate the transducer more frequently shortly after the time for taking a dose of the medication than shortly before the time for taking the next dose in order to collect high resolution data on the rapidity with which the medication takes effect. The doctor attaches the monitor to the patient's wrist and the patient leaves the doctor's office. Over several days, the monitor collects data (step 120) based on the manner in which the doctor programmed the monitor and the manner in which the patient responds to the prompts. After this data collection session, the patient docks the monitor with a local interface unit (similar to the interface unit 13) for downloading the collected data. The local interface unit transmits the data to the host computer (step 130) and the doctor evaluates the patient's condition (step 140) based on the data received by the host computer 12. Based on this evaluation, the doctor might adjust the therapy (step 150) and, based on the adjusted therapy, modify the program of the monitor (step 160). The doctor employs the host computer 12 to generate modified program information and transmit the modified program information to the patient's local interface unit for uploading to the monitor 1. A new data collection session then starts (step 120).

Data may be transmitted between the patient's local interface unit and the host computer 12 using wire-based and/or wireless technology, such as by telephone or over the Internet.

It will be appreciated that the invention is not restricted to the particular embodiment that has been described, and that variations may be made therein without departing from the scope of the invention as defined in the appended claims and equivalents thereof. For example, although the invention has been described with reference to the case in which the timing information stored in the memory 20 directly represents time intervals, it would alternatively be possible to store variables that can be used by an algorithm stored by the controller 22 to calculate time intervals. In both cases described so far, the timing information allows multiple intervals of different duration to be specified, so that the doctor can vary the interval between transducer activations. In a simpler case, the memory might store a single item of timing information, specifying a uniform interval between transducer activations. The uniform interval would typically be 30 minutes, 60 minutes or 120 minutes depending on the resolution required by the doctor for the data collection session. Further, although the invention has been described with reference to a pain management application, it is also applicable to diagnosis and treatment of other subjective or qualitative medical conditions such as depression, anxiety, fatigue, obesity and alcoholism.

What is claimed is:

1. An apparatus to be worn by a user on the user's wrist for recording score values representing a user's subjective rating of a condition, comprising:

a casing having an external surface, a strap for attaching the casing to the user's wrist, a clock within the casing for generating a periodic timing signal, a user interface at said external surface of the casing for entering score values, a transducer within the casing for prompting the user to enter a score value, a time storage device within the casing for storing timing information, a data storage device within the casing for storing time values and related score values, a controller within the casing and coupled to said clock, said time storage device and said transducer for activating said transducer at times indicated by said timing information, and an output means for reading the stored time values and related score values from the data storage device.

2. Apparatus in accordance with claim 1, further comprising an input means for providing said timing information for storing in said time storage device.

3. Apparatus in accordance with claim 2, wherein said timing information comprises discrete time values.

4. Apparatus in accordance with claim 2, wherein said timing information comprises instructions for determining specific time values by execution of an algorithm.

5. Apparatus in accordance with claim 1, further comprising an activity sensor for generating activity data representative of the user's level of physical activity and storing the activity data in the data storage device to be read by said output means.

6. Apparatus in accordance with claim 1, further comprising an activity sensor for generating activity data representative of the user's level of physical activity and storing the activity data and related time values in the data storage device to be read by said output means.

7. A method of administering a therapy to a patient for relieving a medical condition that is reflected by a patient-perceptible symptom, comprising:

prescribing an initial therapy for relieving the medical condition and providing the patient with a monitor to be worn on the user's wrist for collecting subjective data reflecting the patient's perception of the symptom and measuring and collecting objective data reflecting a physical condition of the patient, employing the monitor to collect subjective data reflecting the patient's perception of the symptom and to measure and collect objective data reflecting the physical condition of the patient, transmitting the collected data to an evaluation site, evaluating the patient's medical condition based on the data received at the evaluation site, and, if the evaluation indicates a change in therapy, transmitting a revised therapy to the patient.

8. A method according to claim 7, wherein the medical condition is reflected by pain and the physical condition is level of physical activity of the patient.

9. A method according to claim 7, wherein the medical condition is reflected by depression and the physical condition is level of physical activity of the patient.

10. A method according to claim 7, wherein the physical condition is level of physical activity of the patient.

11. An apparatus to be worn by or secured to a user for recording score values representing a user's subjective rating of a condition, comprising:

a casing having an external surface, a clock within the casing for generating a periodic timing signal, a user interface at said external surface of the casing for entering score values, a transducer within the casing for prompting the user to enter a score value, a time storage device within the casing for storing timing information, a data storage device within the casing for storing time values and related score values, a controller within the casing and coupled to said clock, said time storage device and said transducer for activating said transducer at times indicated by said timing information, an output means for reading the stored time values and related score values from the data storage device, and an activity sensor within the casing for generating activity data representative of the user's level of physical activity and storing the activity data in the data storage device to be read by said output means.

12. Apparatus in accordance with claim 11, wherein the activity sensor stores the activity data and related time values in the data storage device to be read by said output means.

* * * * *